(12) United States Patent
Matsuura et al.

(10) Patent No.: US 10,945,623 B2
(45) Date of Patent: Mar. 16, 2021

(54) HEARTBEAT DETECTION METHOD AND HEARTBEAT DETECTION DEVICE

(71) Applicant: NIPPON TELEGRAPH AND TELEPHONE CORPORATION, Tokyo (JP)

(72) Inventors: Nobuaki Matsuura, Tokyo (JP); Kei Kuwabara, Tokyo (JP); Takayuki Ogasawara, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 43 days.

(21) Appl. No.: 16/080,645

(22) PCT Filed: Feb. 13, 2017

(86) PCT No.: PCT/JP2017/005124
§ 371 (c)(1),
(2) Date: Aug. 28, 2018

(87) PCT Pub. No.: WO2017/150156
PCT Pub. Date: Sep. 8, 2017

(65) Prior Publication Data
US 2019/0069791 A1    Mar. 7, 2019

(30) Foreign Application Priority Data
Feb. 29, 2016    (JP) .............................. JP2016-036766

(51) Int. Cl.
*A61B 5/04*    (2006.01)
*A61B 5/024*    (2006.01)
(Continued)

(52) U.S. Cl.
CPC ........ *A61B 5/04012* (2013.01); *A61B 5/0245* (2013.01); *A61B 5/0452* (2013.01);
(Continued)

(58) Field of Classification Search
CPC . A61B 5/04012; A61B 5/0452; A61B 5/0456; A61B 5/0245; A61B 5/7203; A61B 5/0468; A61B 5/0408; A61B 5/02405
See application file for complete search history.

(56) References Cited

FOREIGN PATENT DOCUMENTS

| JP | H04-341237 A | 11/1992 |
|---|---|---|
| JP | H07-016214 A | 1/1995 |

(Continued)

OTHER PUBLICATIONS

International Search Report and Written Opinion received for PCT Patent Application No. PCT/JP2017/005124, dated Apr. 4, 2017, 11 pages (5 Pages of English Translation and 6 Pages of Original Documents).

(Continued)

*Primary Examiner* — Mark Bockelman
(74) *Attorney, Agent, or Firm* — Womble Bond Dickinson (US) LLP

(57) ABSTRACT

There is provided a heartbeat detection device. The heartbeat detection device includes a time difference value calculation unit (3) configured to calculate a time difference value of sampling data of an electrocardiographic waveform, FIFO buffers (4-1, 4-2) configured to receive the time difference value, a FIFO buffer (4-3) configured to receive an output from the FIFO buffer (4-2), a FIFO buffer (4-4) configured to receive an output from the FIFO buffer (4-3), a minimum value detection unit (5) configured to detect, for each sampling time, a minimum value M out of the time difference value stored in the FIFO buffer (4-2) and the time difference value stored in the FIFO buffer (4-4), and a heartbeat time determination unit (6) configured to set, when a difference value M−a between the minimum value M and (Continued)

an output value a of the FIFO buffer (4-1) is equal to or greater than a threshold, sampling time of the output value a as heartbeat time.

5 Claims, 9 Drawing Sheets

(51) Int. Cl.

| | |
|---|---|
| *A61B 5/0408* | (2006.01) |
| *A61B 5/0456* | (2006.01) |
| *A61B 5/0245* | (2006.01) |
| *A61B 5/0452* | (2006.01) |
| *A61B 5/0468* | (2006.01) |
| *A61B 5/00* | (2006.01) |

(52) U.S. Cl.
CPC ........ *A61B 5/0456* (2013.01); *A61B 5/02405* (2013.01); *A61B 5/0408* (2013.01); *A61B 5/0468* (2013.01); *A61B 5/7203* (2013.01)

(56) References Cited

FOREIGN PATENT DOCUMENTS

| | | |
|---|---|---|
| JP | 2002-078695 A | 3/2002 |
| JP | 2003-000561 A | 1/2003 |
| JP | 2008-104640 A | 5/2008 |

OTHER PUBLICATIONS

International Preliminary Report on Patentability received for PCT Patent Application No. PCT/JP2017/005124, dated Sep. 13, 2018, 10 pages (6 Pages of English Translation and 4 Pages of Original Document).

"ECG Implementation on the TMS320C5515 DSP Medical Development Kit (MDK) with the ADS1298 ECG-FE", Texas Instruments Incorporated, http://www.ti.com/lit/an/sprabj1/sprabj1.pdf, 2011.

HEARTBEAT DETECTION METHOD AND HEARTBEAT DETECTION DEVICE

TECHNICAL FIELD

The present invention relates to a technique for extracting biological information such as a heartbeat interval (R-R interval) from an electrocardiographic waveform and, more particularly, to a heartbeat detection method and heartbeat detection device for detecting a heartbeat while acquiring an electrocardiographic waveform in real time.

BACKGROUND ART

A heart rate or a fluctuation in heart rate is biological information obtained from an Electrocardiogram (ECG), which is an index of exercise intensity in a sports-related field and is used for evaluation of the autonomic function in daily life or a resting state. An ECG waveform is obtained by observing the electrical activity of a heart, and is measured by attaching electrodes to a body surface. As an ECG waveform lead system, that is, an electrode arrangement, there are various types. For example, when electrodes are arranged at, for example, left and right chests to sandwich the heart, a stable waveform having a large amplitude is obtained. When performing data processing such as heartbeat detection for an ECG waveform, the ECG waveform is processed as a discrete data string sampled at a predetermined time interval.

FIG. 9 shows an example of a general ECG waveform. The ECG waveform is formed from continuous heartbeat waveforms, and one heartbeat waveform is formed from components such as P, Q, R, S, and T waves reflecting the activities of atriums and ventricles. Among them, the R wave is generated in accordance with cardiac contraction (depolarization of the ventricular muscle), and has a large amplitude. Therefore, a heartbeat is often detected with reference to the R wave. In particular, it becomes easy to detect a heartbeat by obtaining the time difference of the sampling data string of the ECG waveform and emphasizing an abrupt change from the R wave to the S wave like peaks. A heartbeat interval for each heartbeat is called an R-R interval, and is used as the primary index of a heartbeat fluctuation.

As related heartbeat detection methods, the following literatures are known. Patent literature 1 discloses an arrangement for removing the fluctuation of the baseline of an ECG waveform. Patent literature 2 discloses an arrangement of recognizing an R wave using a threshold based on an amplitude between the peak and valley of a waveform.

Non-patent literature 1 describes a method of obtaining the R-R interval or the like based on a change in value obtained by calculating the time difference of an ECG waveform. More specifically, the absolute value of the difference between the (n+1)th sampling value and the (n−1)th sampling value is obtained, time at which the value exceeds a given threshold is recorded, and then the interval between two successive times at each of which the threshold is exceeded is set as an R-R interval.

However, the above-described heartbeat detection method has the following problem. In the method of detecting a heartbeat using the time difference value of the ECG waveform based on the fact that the time difference value exceed the given threshold, a problem may arise in which a heartbeat having a small amplitude of the time difference value is missed or noise that is not a heartbeat is erroneously detected as a heartbeat.

FIG. 10 is a timing chart for explaining the problem of the related heartbeat detection method, showing some of sampling data of an ECG waveform. In FIG. 10, the abscissa represents time and the ordinate represents the cardiac potential [μV].

FIG. 11 is a timing chart showing the time difference value "(n+1)th sampling value−(n−1)th sampling value" of the ECG waveform shown in FIG. 10, in which the abscissa represents time and the ordinate represents the difference value [μV] of the cardiac potential. By obtaining the time difference of the ECG waveform, it becomes obvious that a downward peak along with an abrupt decrease in cardiac potential from the R wave to the S wave appears in accordance with the heartbeat rhythm.

In FIG. 11, each ♦ mark 11 indicates heartbeat time detected based on a threshold TH for the above downward peak in accordance with the method described in non-patent literature 1 and an R-R interval [ms] based on the heartbeat time.

On the ECG waveform shown in FIG. 10, the fluctuation of the baseline or superimposition of noise is observed. As a result, in FIG. 11, a peak having a small amplitude fails to be detected (a portion 12 in FIG. 11) and noise is detected as a heartbeat (a ♦ mark 13 in FIG. 11).

RELATED ART LITERATURE

Patent Literature

Patent Literature 1: Japanese Patent Laid-Open No. 2002-78695
Patent Literature 2: Japanese Patent Laid-Open No. 2003-561

Non-Patent Literature

Non-Patent Literature 1: "ECG Implementation on the TMS320C5515 DSP Medical Development Kit (MDK) with the ADS1298 ECG-FE", Texas Instruments Incorporated, http://www.ti.com/lit/an/sprabj1/sprabj1.pdf, 2011

DISCLOSURE OF INVENTION

Problem to be Solved by the Invention

The present invention has been made in consideration of the above problems, and has as its object to provide a heartbeat detection method and heartbeat detection device capable of appropriately detecting a heartbeat and time of the heartbeat even from ECG waveform data in which am amplitude fluctuates or on which noise is superimposed.

Means of Solution to the Problem

According to the present invention, there is provided a heartbeat detection method including a first step of calculating, for each sampling time, a time difference value of sampling data from a sampling data string of an electrocardiographic waveform of a living body, a second step of inputting the time difference value to a first FIFO buffer and a second FIFO buffer, a third step of inputting an output from the second FIFO buffer to a third FIFO buffer, and inputting an output from the third FIFO buffer to a fourth FIFO buffer, a fourth step of detecting, for each sampling time, a minimum value M out of the time difference value stored in the second FIFO buffer and the time difference value stored in the fourth FIFO buffer, and a fifth step of calculating, for each sampling time, a difference value M−a between the minimum value M detected in the fourth step and an output value a of the first FIFO buffer, and setting, when the difference value M−a is equal to or greater than a threshold, the sampling time of the output value a as a heartbeat time.

According to the present invention, there is also provided a heartbeat detection device including a time difference value calculation unit configured to calculate, for each sampling time, a time difference value of sampling data from a sampling data string of an electrocardiographic waveform of a living body, a first FIFO buffer and a second FIFO buffer each configured to receive the time difference value calculated by the time difference value calculation unit, a third FIFO buffer configured to receive an output from the second FIFO buffer, a fourth FIFO buffer configured to receive an output from the third FIFO buffer, a minimum value detection unit configured to detect, for each sampling time, a minimum value M out of the time difference value stored in the second FIFO buffer and the time difference value stored in the fourth FIFO buffer, and a heartbeat time determination unit configured to calculate, for each sampling time, a difference value M−a between the minimum value M detected by the minimum value detection unit and an output value a of the first FIFO buffer, and set, when the difference value M−a is equal to or greater than a threshold, the sampling time of the output value a as a heartbeat time.

Effect of the Invention

According to the present invention, a time difference value of sampling data is calculated for each sampling time from a sampling data string of an electrocardiographic waveform, the time difference value is input to a first FIFO buffer and a second FIFO buffer, an output from the second FIFO buffer is input to a third FIFO buffer, an output from the third FIFO buffer is input to a fourth FIFO buffer, a minimum value M out of the time difference value stored in the second FIFO buffer and the time difference value stored in the fourth FIFO buffer is detected, and when a difference value M−a between the minimum value M and an output value a of the first FIFO buffer is equal to or greater than a threshold, the sampling time of the output value a is set as a heartbeat time. The time difference value of the sampling data of the electrocardiographic waveform derived from an R wave has a sharp downward peak, and sticks out in the surroundings. In the present invention, it is possible to appropriately detect the peak of the R wave by confirming the clearance of the time difference value of the sampling data in a peripheral region with respect to the peak. As a result, in the present invention, it is possible to appropriately detect the peak of the R wave of the time difference value with sensitivity to a width and durability against an amplitude fluctuation while processing the sampling data string of the electrocardiographic waveform in real time.

BEST MODE FOR CARRYING OUT THE INVENTION

First Embodiment

Figure 1:
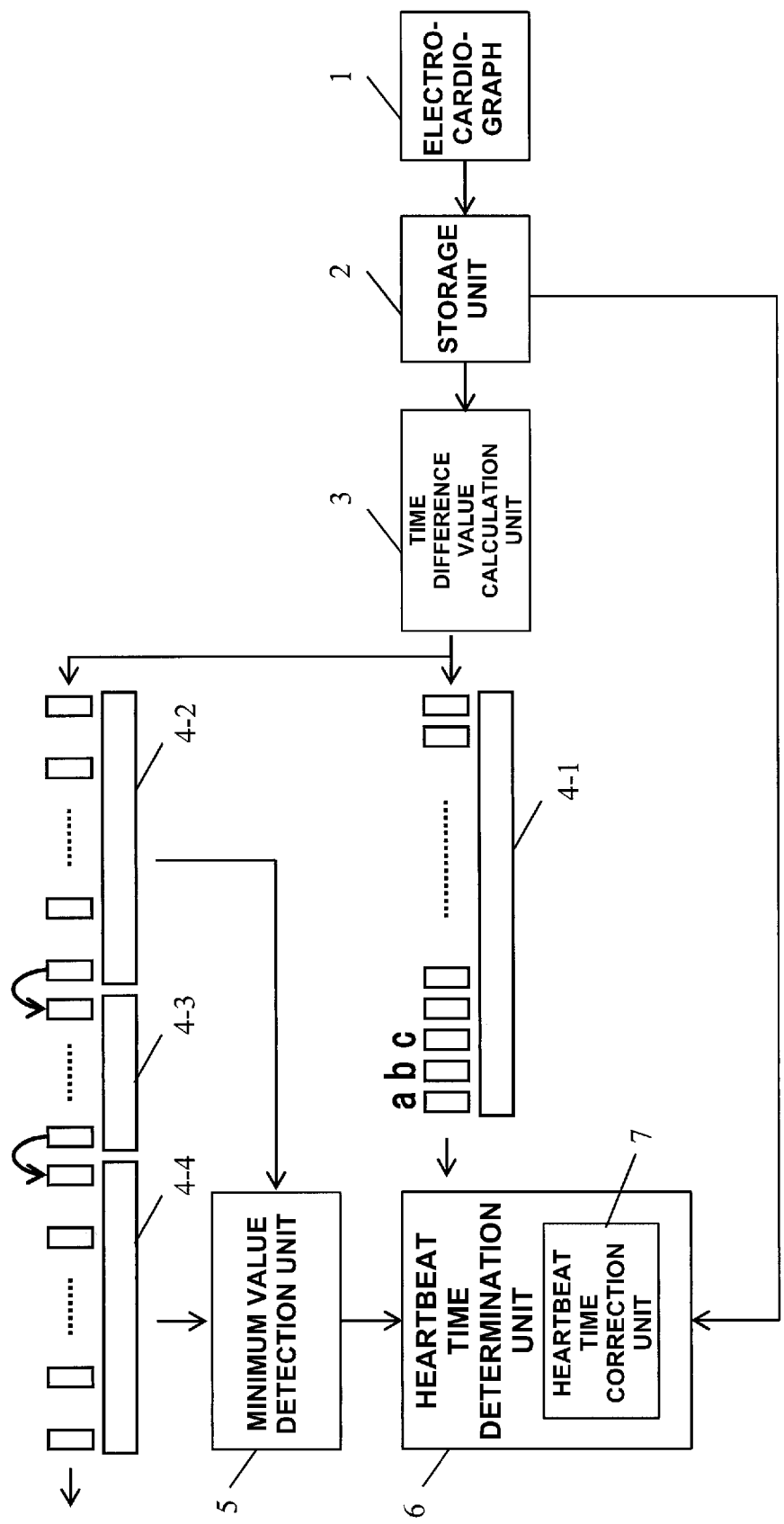
FIG. 1 is a block diagram showing the arrangement of a heartbeat detection device according to the first embodiment of the present invention.
Figure 2:
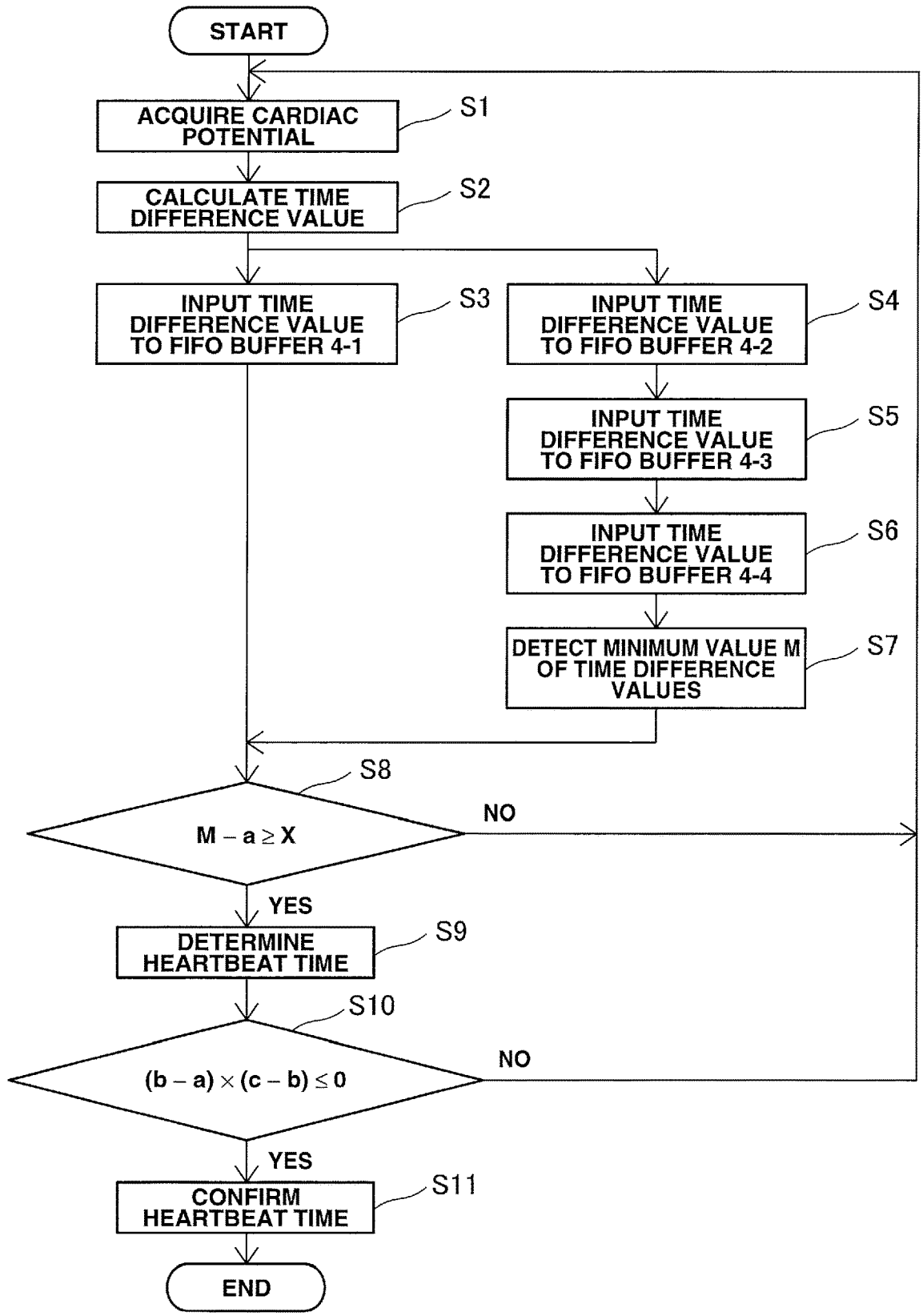
FIG. 2 is a flowchart for explaining a heartbeat detection method according to the first embodiment of the present invention.

The embodiment of the present invention will be described below with reference to the accompanying drawings. FIG. 1 is a block diagram showing the arrangement of a heartbeat detection device according to the first embodiment of the present invention. FIG. 2 is a flowchart for explaining a heartbeat detection method according to this embodiment. The heartbeat detection device includes an electrocardiograph 1 that outputs the sampling data string of an ECG waveform, a storage unit 2 that stores sampling data string of the ECG waveform and sampling time information, a time difference value calculation unit 3 that calculates, for each sampling time, the time difference value of sampling data from the sampling data string of the ECG waveform, FIFO buffers (First In, First Out) 4-1 and 4-2 each of which receives the time difference value calculated by the time difference value calculation unit 3, a FIFO buffer 4-3 that receives an output from the FIFO buffer 4-2, a FIFO buffer 4-4 that receives an output from the FIFO buffer 4-3, a minimum value detection unit 5 that detects, for each sampling time, a minimum value M out of the time difference value stored in the FIFO buffer 4-1 and that stored in the FIFO buffer 4-4, and a heartbeat time determination unit 6 that sets, when a difference value M−a between the minimum value M and an output value a of the FIFO buffer 4-1 is equal to or larger than a threshold X, sampling time of the output value a as heartbeat time.

The heartbeat detection method according to this embodiment will be described below. A procedure of detecting a single heartbeat and obtaining the time when the heartbeat occurred, that is a heartbeat time, will be explained. By repeating calculation of heartbeat time for the period of ECG waveform data, time-series data of heartbeat times are obtained.

In this embodiment, D(i) represents a data string obtained by sampling the ECG waveform where i (i=1, 2, . . . )

represents a number assigned to a single sampling data. The larger the number i, the later the sampling time is, as a matter of course.

The electrocardiograph 1 measures the ECG waveform of a living body (human body) (not shown), and outputs the sampling data string D(i) of the ECG waveform. At this time, the electrocardiograph 1 outputs the sampling data string by adding sampling time information to each sampling data. Note that a practical method of measuring the ECG waveform is a well-known technique and a detailed description thereof will be omitted.

The storage unit 2 stores the sampling data string D(i) of the ECG waveform and the sampling time information, which have been output from the electrocardiograph 1.

To calculate a time difference value Y(i) of the sampling data D(i), the time difference value calculation unit 3 acquires, from the storage unit 2, data D(i+1) that is obtained after carrying out a single sampling operation of the sampling data D(i), and data D(i−1) that is obtained prior to carrying out the single sampling operation of the sampling data D(i) (step S1 of FIG. 2). Then, the time difference value calculation unit 3 calculates the time difference value Y(i) of the sampling data D(i) for each sampling time (step S2 of FIG. 2) by:

$$Y(i)=D(i+1)-D(i-1) \quad (1)$$

The time difference value calculation unit 3 inputs the calculated time difference value Y(i) to the FIFO buffer 4-1 for each sampling time (step S3 of FIG. 2). The input value is held in the FIFO buffer 4-1, and is used for evaluation after a time corresponding to the size of the FIFO buffer 4-1 (a delay time from when the time difference value is input to the FIFO buffer 4-1 until it is output) elapses.

The time difference value calculation unit 3 inputs the calculated time difference value Y(i) to the FIFO buffer 4-2 (step S4 of FIG. 2). Note that a data acquisition interval can be set to relatively longer intervals of about 10 ms. Therefore, when, for example, the sampling interval of the ECG waveform is 5 ms, the time difference value calculation unit 3 inputs the time difference value to the FIFO buffer 4-2 once every two sampling operations.

An output from the FIFO buffer 4-2 is input to the FIFO buffer 4-3 (step S5 of FIG. 2), and an output from the FIFO buffer 4-3 is input to the FIFO buffer 4-4 (step S6 of FIG. 2). The FIFO buffers 4-2 to 4-4 are used to obtain the minimum value (floor level) of the time difference values within a given time range.

A time interval L3 (a delay time from when the time difference value is input to the FIFO buffer 4-3 until it is output) corresponding to the size of the FIFO buffer 4-3 needs to be long enough for the width (about 10 ms) of the peak of an R wave, and is preferably about 25 ms. Furthermore, a time interval L2 (a delay time from when the time difference value is input to the FIFO buffer 4-2 until it is output) corresponding to the size of the FIFO buffer 4-2 and a time interval L4 (a delay time from when the time difference value is input to the FIFO buffer 4-4 until it is output, where L2=L4) corresponding to the size of the FIFO buffer 4-4 are appropriately about 100 ms. A time interval L1 corresponding to the size of the FIFO buffer 4-1 is given by L1=L2+L3/2. Therefore, using the above numerical values, L1 is 112.5 ms. By setting L1=L2+L3/2 and L2=L4, it is possible to evaluate whether the output value a is smaller than the minimum value M by the threshold X or more with respect to time of the output from the FIFO buffer 4-1 within a range of −(L2+L3/2) to −(L3/2) and a range of (L3/2) to (L2+L3/2).

The minimum value detection unit 5 detects, for each sampling time, the minimum value M out of the time difference value stored in the FIFO buffer 4-2 and that stored in the FIFO buffer 4-4 (step S7 of FIG. 2).

The heartbeat time determination unit 6 calculates, for each sampling time, the difference value M−a between the minimum value M detected by the minimum value detection unit 5 and the output value a of the FIFO buffer 4-1. When the difference value M−a is equal to or greater than the threshold X, that is, inequality (2) below is true (YES in step S8 of FIG. 2), sampling time of the output value a is set as a heartbeat time (step S9 of FIG. 2).

$$M-a \geq X \quad (2)$$

Note that the output value a is a time difference value at the time interval L1 earlier than when the most recent time difference value is calculated by the time difference value calculation unit 3. Sampling time information of the output value a can be acquired from the storage unit 2.

Figure 3:
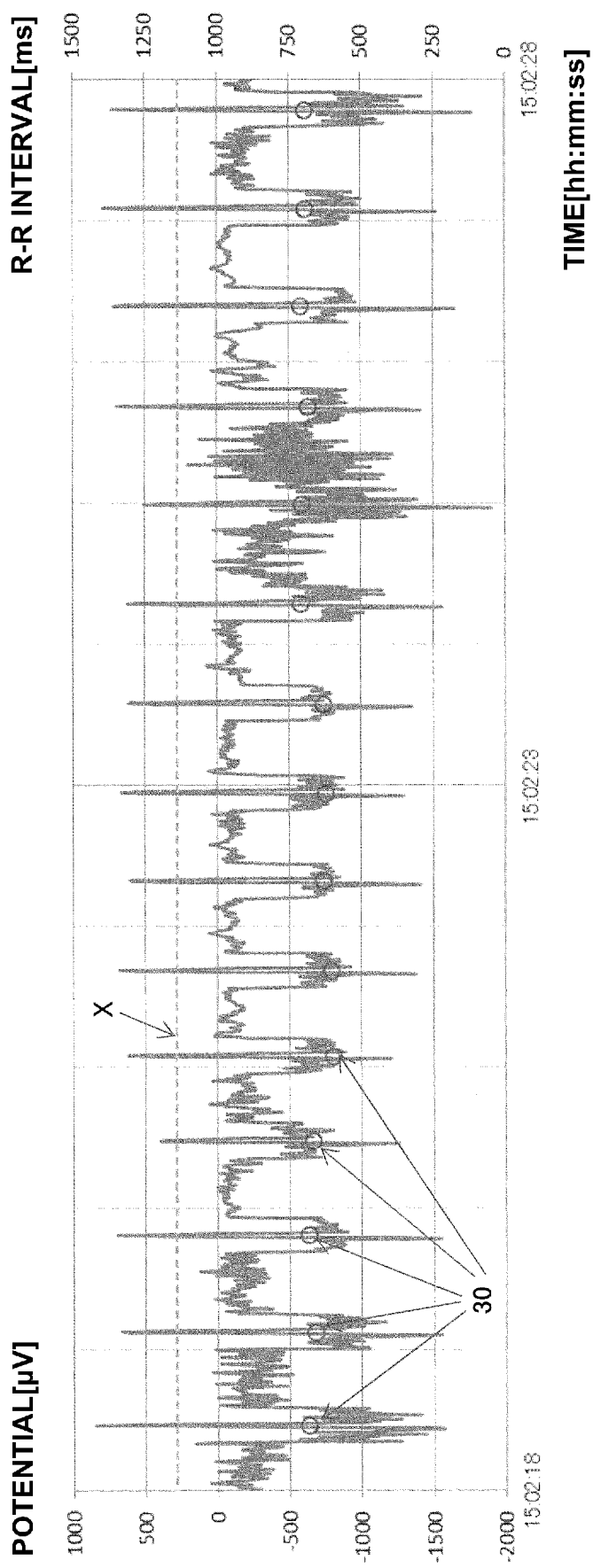
FIG. 3 is a timing chart obtained by plotting the difference between a minimum value out of a time difference value stored in the second FIFO buffer and that stored in the fourth FIFO buffer and an output value of the first FIFO buffer.
Figure 10:
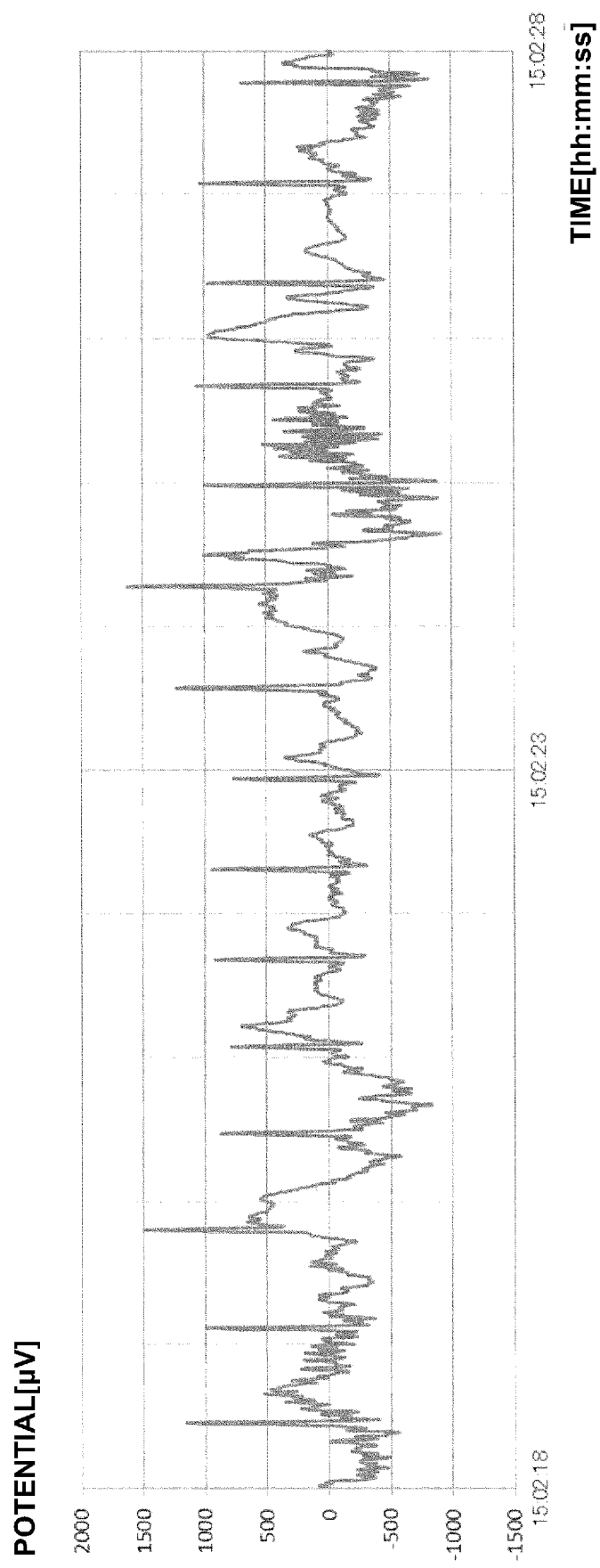
FIG. 10 is a timing chart showing one example of sampling data of an electrocardiographic waveform.

FIG. 3 is a timing chart obtained by plotting, on the time axis, the value of the difference (M−a) between the minimum value M and the output value a of the FIFO buffer 4-1 with respect to the sampling data of the ECG waveform shown in FIG. 10. The value of (M−a) has a sharp upward peak in accordance with an R wave, and is a value close to 0 or a negative value in portions other than the R waves. Therefore, it is possible to detect an R wave by detecting time when the value of (M−a) becomes equal to or greater than the threshold X. In FIG. 3, each 0 mark 30 indicates heartbeat time detected by inequality (2) and an R-R interval [ms]. It is apparent that the R wave can be detected appropriately by the method according to this embodiment.

Furthermore, a heartbeat time correction unit 7 in the heartbeat time determination unit 6 determines whether the increase/decrease of the output value a of the FIFO buffer 4-1, a value b stored in the FIFO buffer 4-1 that is obtained after carrying out a single sampling operation of the output value a, and a value c stored in the FIFO buffer 4-1 that is obtained after carrying out two sampling operations of the output value a, is inverted or not. That is, whether the increase/decrease of these temporally successive three values is inverted or not is determined (step S10 of FIG. 2). More specifically, the heartbeat time correction unit 7 evaluates true/false of inequality (3) below.

$$(b-a) \times (c-b) \leq 0 \quad (3)$$

When inequality (3) is true (YES in step S10), the heartbeat time correction unit 7 determines that a peak at the value b obtained after carrying out a single sampling operation of the output value a of the FIFO buffer 4-1 is to be the peak of an R wave, and confirms that the sampling time of the value b as a heartbeat time, instead of the heartbeat time determined in the step S9 (step S11 of FIG. 2). When inequalities (2) and (3) are satisfied for the output value a of the FIFO buffer 4-1, M−b≥X is also satisfied for the value b. That is, sampling time of the value b is more appropriate as heartbeat time than the sampling time of the output value a. Thus, in this embodiment, it is possible to specify heartbeat time more precisely.

Note that even if inequality (2) is satisfied and inequality (3) is not satisfied, the heartbeat time is determined by the processing in the step S9. However, this heartbeat time is corrected by the processing in the step S11 when inequalities (2) and (3) are satisfied, thereby confirming the heartbeat time.

Furthermore, while the peak of the R wave for the time difference value is located in a convex downward curve, inequality (3) is true even for the peak at the value b, which is located in a convex upward curve. However, this does not cause any problems since inequality (2) is always false for the peak at the value b, which is located in a convex upward curve.

When determined as NO in the step S8 or S10, the process returns to the step S1 to change the processing target to the sampling data D(i) of the next sampling time. Similarly, when the heartbeat time is confirmed in the step S11, the process returns to the step S1 to change the processing target to the sampling data D(i) of the next sampling time.

By repeating the processes in the steps S1 to S11, time-series data of the heartbeat time is obtained.

Figure 4:
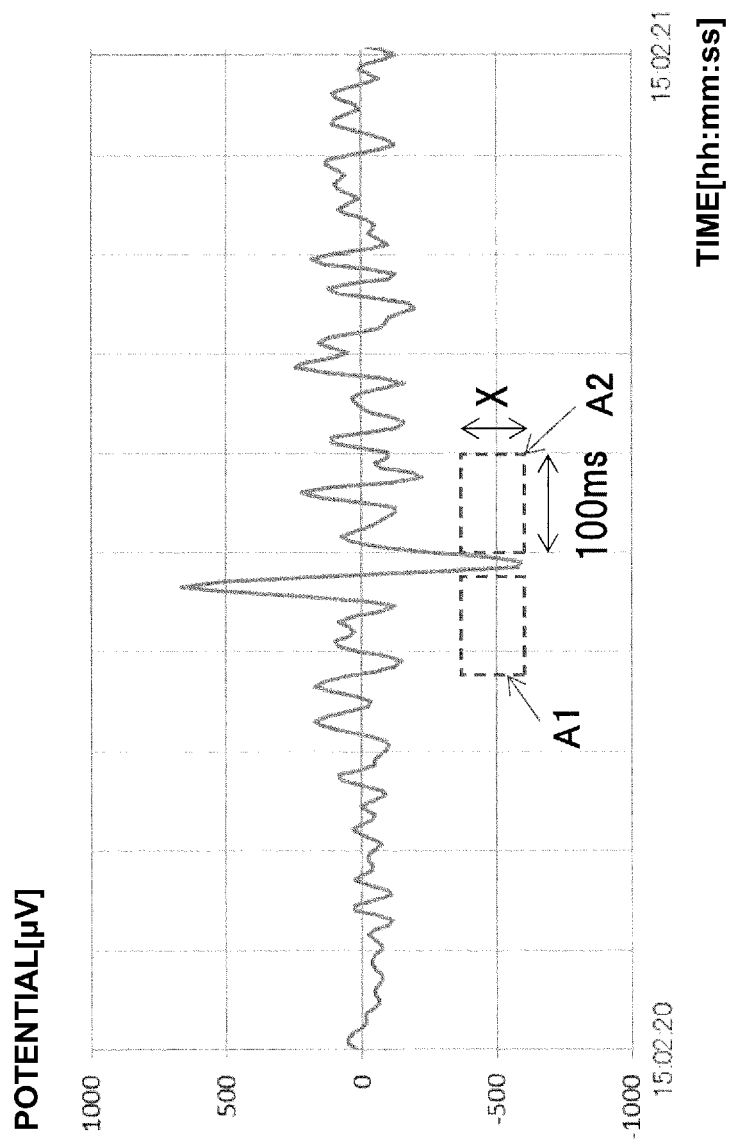
FIG. 4 is an enlarged timing chart showing a portion where an R wave fails to be detected by the related heartbeat detection method.
Figure 11:
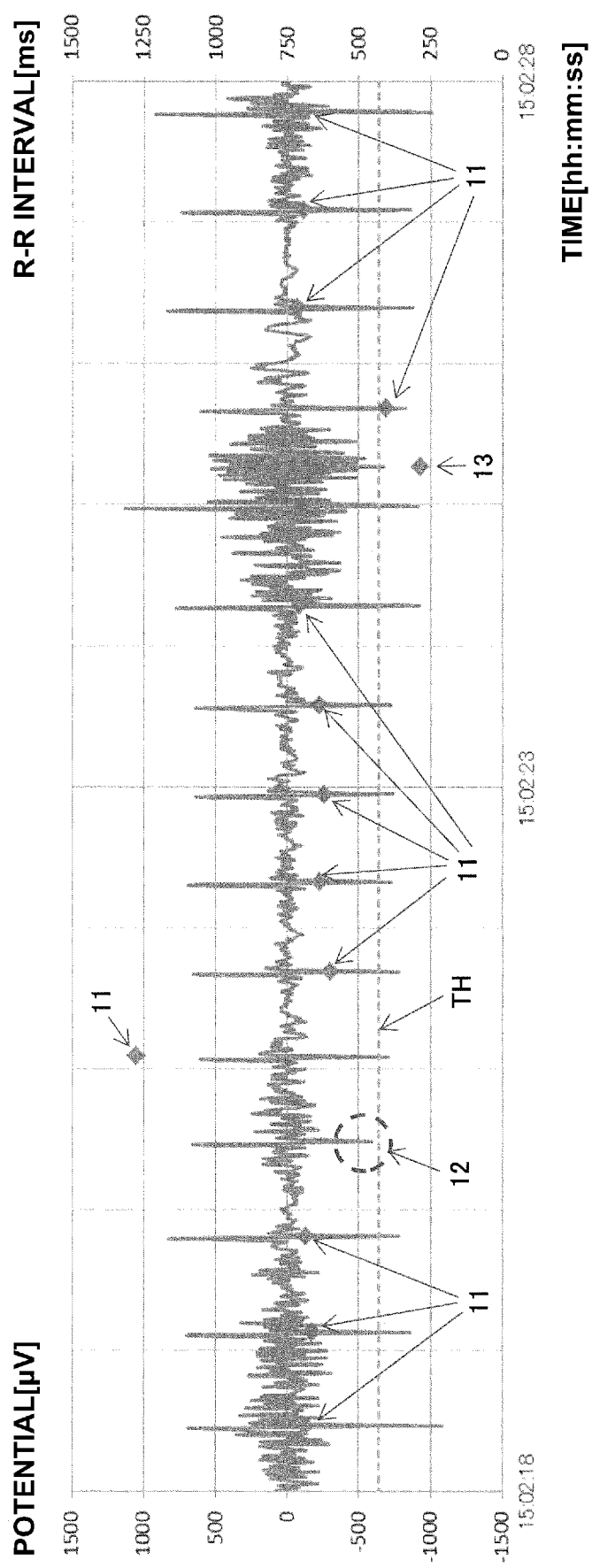
FIG. 11 is a timing chart showing the time difference value of the electrocardiographic waveform shown in FIG. 10.

FIG. 4 is an enlarged timing chart showing a portion (a portion 12 in FIG. 11) where an R wave fails to be detected by the related heartbeat detection method described with reference to FIG. 11. According to this embodiment, as for the time at the peak of the time difference value, a clearance A1 having a time range of −112.5 ms to −12.5 ms (a time range determined by L4+L3/2) and a height X, and a clearance A2 having a time range of 12.5 ms to 112.5 ms (a time range determined by L2+L3/2) and the height X are set. That is, the peak of the time difference value having the clearances A1 and A2 is detected as an R wave.

Figure 5:
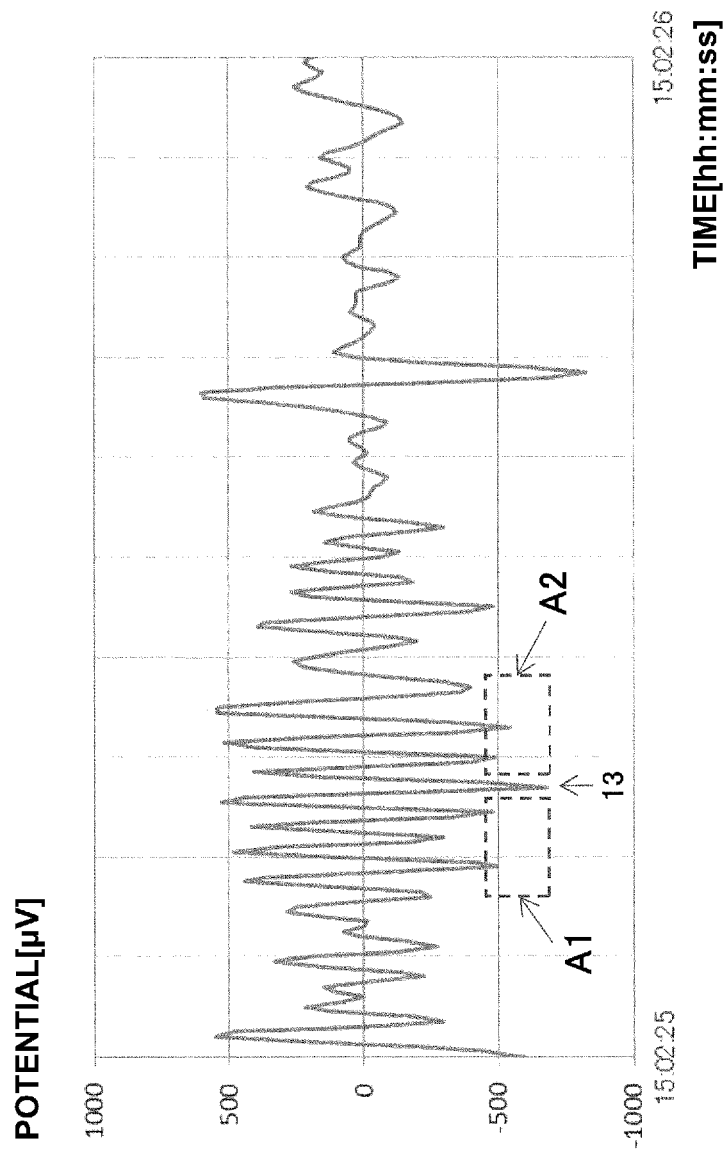
FIG. 5 is an enlarged timing chart showing a portion where noise is erroneously detected as an R wave by the related heartbeat detection method.

Conversely, FIG. 5 is an enlarged timing chart showing a portion (a portion 13 in FIG. 11) where noise is erroneously detected as an R wave by the related heartbeat detection method described with reference to FIG. 11. According to this embodiment, as described similarly above, ranges A1 and A2 are set for the peak of the time difference value at a position 13 in FIG. 5. However, surrounding noise is included in this range, and thus no clearances are secured (inequality (2) is not satisfied). Therefore, according to the method of this embodiment, the peak at the position 13 is not detected as an R wave.

Figure 6:
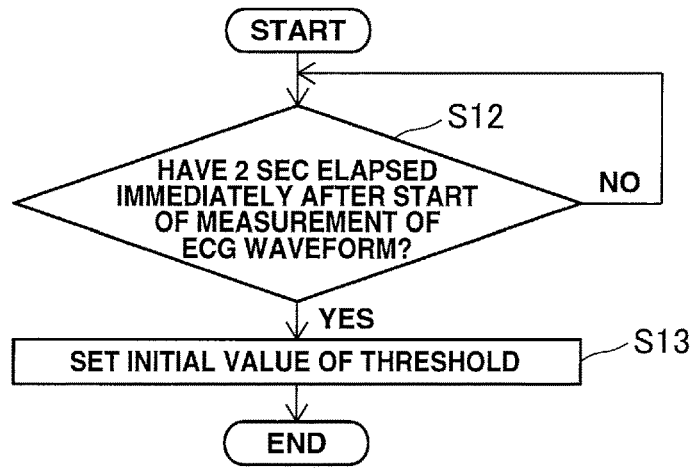
FIG. 6 is a flowchart for explaining processing of setting the initial value of a threshold in the heartbeat detection method according to the first embodiment of the present invention.

The heartbeat time determination unit 6 sets the initial value of the threshold X based on the maximum value of (M−a) for 2 sec immediately after the start of measurement of the ECG waveform without detecting a heartbeat during that period (steps S12 and S13 of FIG. 6). When $(M-a)_{max}$ represents the maximum value of (M−a) for 2 sec immediately after the start of measurement of the ECG waveform, the heartbeat time determination unit 6 sets the initial value of the threshold X by:

$$X = \alpha \times (M-a)_{max} \quad (4)$$

α represents a predetermined coefficient (0<α 1). In this way, it is possible to set the initial value of the threshold X appropriately using the value of (M−a) during a period immediately after the start of measurement of the ECG waveform, regardless of the characteristics of electrodes for obtaining the ECG waveform, the individual difference, and the like.

Figure 7:
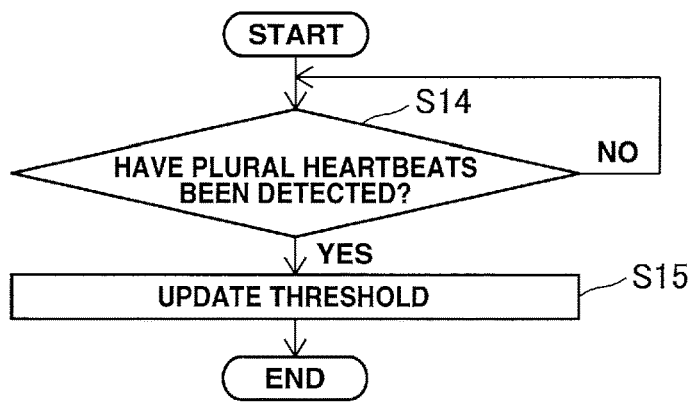
FIG. 7 is a flowchart for explaining processing of updating the threshold in the heartbeat detection method according to the first embodiment of the present invention.

Furthermore, the heartbeat time determination unit 6 may update the threshold X using the latest average value of (M−b) obtained when a heartbeat is detected by the processes in the steps S10 and S11. When $(M-b)_{ave}$ represents the average value of values of (M−b) obtained by detecting a plurality (for example, five) of the most recent heartbeats, the heartbeat time determination unit 6 updates the threshold X (steps S14 and S15 of FIG. 7) by:

$$X = \alpha \times (M-b)_{ave} \quad (5)$$

By updating the threshold X in this way, it is possible to reflect the trend of the ECG waveform. When performing the determination processing in the step S8, the heartbeat time determination unit 6 may update the threshold X by using the equation (5) by setting, as $(M-b)_{ave}$, the average value of the values of (M−b) obtained by heartbeats that have already been detected. This can stabilize the transition of the threshold X.

Second Embodiment

Figure 8:
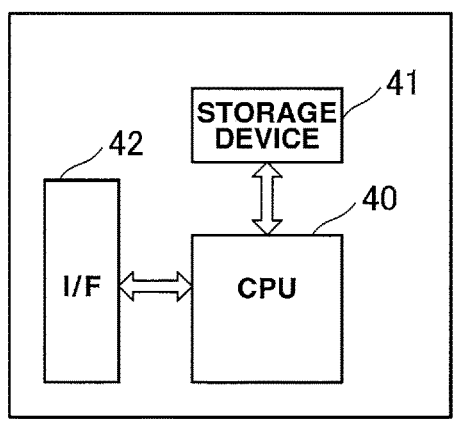
FIG. 8 is a block diagram showing an example of the arrangement of a computer for implementing the heartbeat detection device according to the first embodiment of the present invention.
Figure 9:
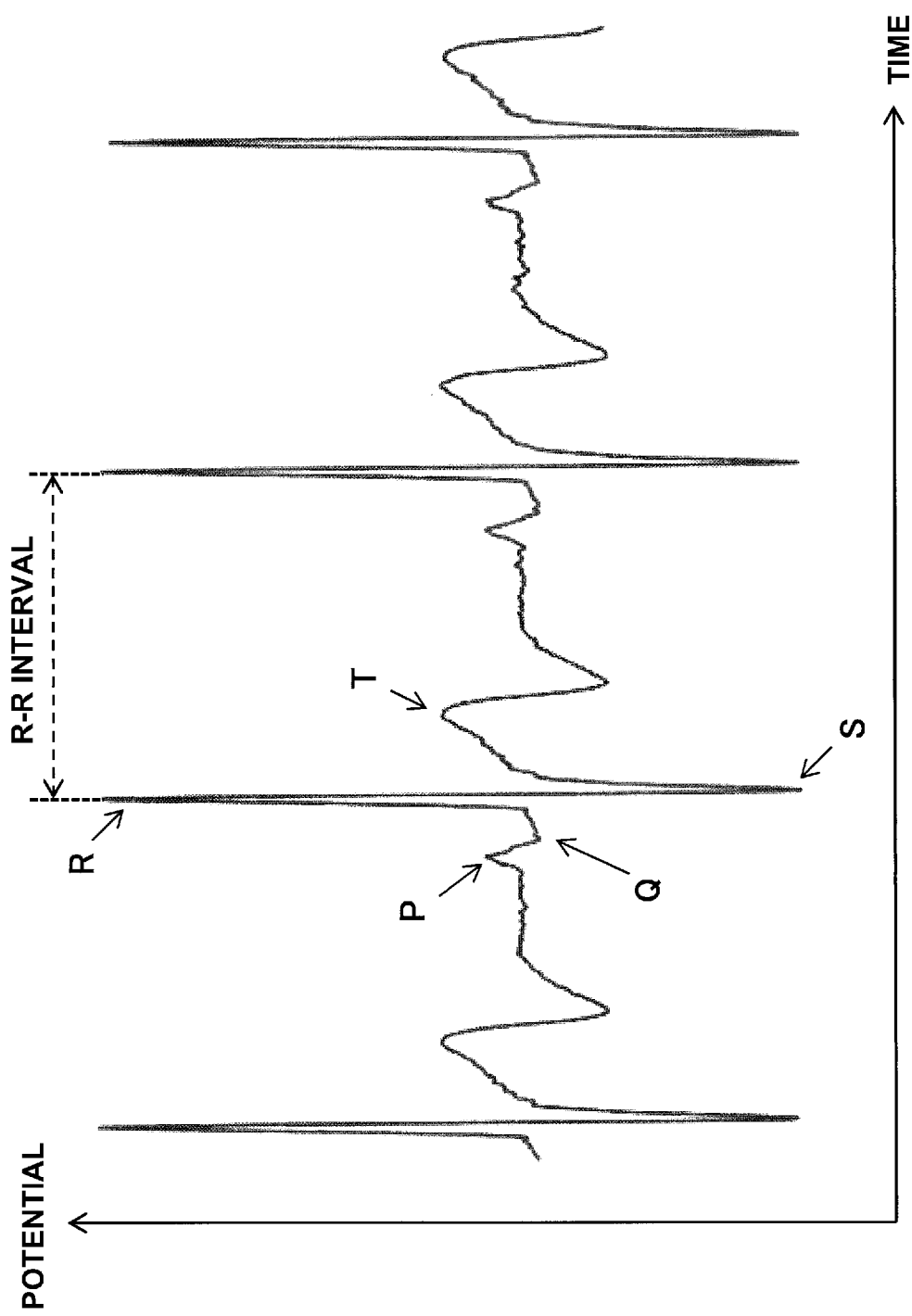
FIG. 9 is a timing chart showing an example of an electrocardiographic waveform.

The storage unit 2, time difference value calculation unit 3, FIFO buffers 4-1 to 4-4, minimum value detection unit 5, heartbeat time determination unit 6, and heartbeat time correction unit 7 of the heartbeat detection device described in the first embodiment can be implemented by a computer including a CPU (Central Processing Unit), a storage device, and an interface, and a program for controlling these hardware resources. FIG. 8 shows an example of the arrangement of this computer. The computer includes a CPU 40, a storage device 41, and an interface device (to be referred to as an I/F hereinafter) 42. The I/F 42 is connected to the electrocardiograph 1 and the like. In this computer, a program for implementing the heartbeat detection method of the present invention is provided while being recorded on a recording medium such as a flexible disk, CD-ROM, DVD-ROM, or memory card, and stored in the storage device 41. The CPU 40 executes the processing described in the first embodiment in accordance with the program stored in the storage device 41.

INDUSTRIAL APPLICABILITY

The present invention is applicable to a technique of detecting heartbeats of a living body.

EXPLANATION OF THE REFERENCE NUMERALS AND SIGNS

1 . . . electrocardiograph, 2 . . . storage unit, 3 . . . time difference value calculation unit, 4-1-4-4 . . . FIFO buffer, 5 . . . minimum value detection unit, 6 . . . heartbeat time determination unit, 7 . . . heartbeat time correction unit

The invention claimed is:

1. A heartbeat detection device comprising:
an electrocardiograph having electrodes attached on a surface of a living body, and configured to output a sampling data string obtained by sampling at a predetermined time interval an electrocardiographic waveform of the living body;
a storage device configured to store the sampling data string output by the electrocardiograph;
a first FIFO (First-In, First-Out) buffer memory configured to store a first value input for a first delay time L1 before outputting the first value;
a second FIFO buffer memory configured to store a second value input for a second delay time L2 before outputting the second value;
a third FIFO buffer memory configured to receive the second value output from the second FIFO buffer memory as a third value input and store the third value for a third delay time L3 before outputting the third value;
a fourth FIFO buffer memory configured to receive an output from the third FIFO buffer memory as a fourth value input and store the fourth value for a fourth delay time L4 before outputting the fourth value; and
a processing circuit, wherein the processing circuit comprises:
a time difference value calculation circuit configured to read out the sampling data string, calculate, for each sampling time, a time difference value between consecutive sampling data of the sampling data string, and sequentially input the time difference value to both of the first FIFO buffer memory and the second FIFO buffer memory;

a minimum value detection circuit configured to detect, for each sampling time, a minimum value M out of a plurality of time difference values stored in the second FIFO buffer memory and the fourth FIFO buffer memory; and a heartbeat time determination circuit configured to calculate, for each sampling time, a difference value M−a between the minimum value M detected by the minimum value detection circuit and an output value a of the first FIFO buffer memory, compare the difference value M−a to a threshold, and determine, when the difference value M−a is equal to or greater than the threshold, the sampling time associated with the output value a as a heartbeat time, wherein each of the first delay time L1, the second delay time L2, the third delay time L3 and the fourth delay time L4 is an integer multiple of the predetermined time interval to produce the sampling data string of the electrocardiographic waveform.

2. The heartbeat detection device according to claim 1, further comprising a heartbeat time correction circuit configured to compare the output value a to a time difference value b, which is a consecutive value after the output value a and stored in the first FIFO buffer memory, and the time difference value b to a time difference value c, which is a consecutive value after the time difference value b and stored in the first FIFO buffer memory, and determine, when an increase and decrease from the time difference value b to the time difference value c is reverse to an increase and decrease from the output a to the time difference value b, a sampling time associated with the value b as the heartbeat time, instead of the heartbeat time determined by the heartbeat time determination circuit.

3. The heartbeat detection device according to claim 2, wherein the heartbeat time determination circuit updates the threshold based on an average value of difference values M−b, each of the difference values M−b is a different value between the minimum value M and the time difference value b when the heartbeat time is determined using the output value a, the time difference value b, and the time difference value c.

4. The heartbeat detection device according claim 1, wherein
the first delay time L1, the second delay time L2, the third delay time L3 and the fourth delay time L4 satisfy relations L1=L2+L3/2 and L2=L4.

5. The heartbeat detection device according to claim 1, wherein the heartbeat time determination circuit sets an initial value of the threshold based on the difference value M−a during a predetermined period immediately after a start of measurement of the electrocardiographic waveform.

* * * * *